United States Patent [19]

Parker et al.

[11] 4,260,832

[45] Apr. 7, 1981

[54] ALKYLATION OF 2,6-DI-TERT-ALKYLPHENOLS WITH ALKANEDIOLS

[75] Inventors: Dane K. Parker, Massillon; Richard H. Kline, Silver Lake, both of Ohio

[73] Assignee: The Goodyear Tire & Rubber Company, Akron, Ohio

[21] Appl. No.: 89,062

[22] Filed: Oct. 29, 1979

[51] Int. Cl.$^3$ .............................................. C07C 39/06
[52] U.S. Cl. ...................................... 568/784; 568/790
[58] Field of Search ................................. 568/790, 784

[56] References Cited

U.S. PATENT DOCUMENTS

| | | | |
|---|---|---|---|
| 2,660,610 | 11/1953 | Erchak | 568/790 |
| 2,841,623 | 7/1958 | Norton et al. | 568/785 |
| 2,841,624 | 7/1958 | Norton et al. | 568/784 |
| 3,860,664 | 1/1975 | Yates | 568/905 |
| 3,919,333 | 11/1975 | Wollensak | 568/790 |

*Primary Examiner*—Joseph E. Evans
*Attorney, Agent, or Firm*—D. O. Nickey

[57] ABSTRACT

There is a process disclosed for alkylating the nucleus of a phenol, said process comprising reacting an $\alpha$, $\omega$-alkanediol containing from 3 to 8 carbon atoms with a phenol having an unsubstituted nuclear position para to the phenolic hydroxyl group; said phenol being selected from the group of alkylated phenols having tertiary alkyl groups of 4 to 8 carbon atoms in both positions ortho to the phenolic hydroxyl group, in the presence of an alkali metal hydroxide or alkoxide or alkali metal at a temperature from 200° to 300° C. while continuously removing the water by-product as it forms and obtaining as a product said phenol having a primary hydroxy terminated alkyl group of 3 to 8 carbon atoms in said para position.

13 Claims, No Drawings

ALKYLATION OF 2,6-DI-TERT-ALKYLPHENOLS WITH ALKANEDIOLS

TECHNICAL FIELD

Phenols are alkylated by reaction with alkane diols containing 3 to 8 carbon atoms in the presence of alkali metal hydroxides, alkoxides or metallic sodium. The present invention specifically relates to an improved method for the preparation of ω-(3,5-di-tert-alkyl-4-hydroxyphenyl) alkanols.

BACKGROUND ART

Alkylated phenols are useful as antioxidants in a broad range of organic materials. In the past they have been prepared by various means such as the reaction of an appropriate phenol with an olefin or an alkyl halide in the presence of an acid or metal halide Friedel-Crafts catalyst.

In a series of Russian articles (I. S. Belostotskaya and V. V. Ershov, *Bulletin of the Academy of Science*, U.S.S.R. 765 1964 and Ibid at 1274, 1965) a tedious nine-step method is outlined for the preparation of 4-(4-hydroxy-3,5-di-tert-butylphenyl)butanol.

According to another method phenols are alkylated with olefins selectively in an ortho position using an aluminum phenoxide catalyst, U.S. Pat. No. 2,831,989. Phenols have also been alkylated by aldehydes in an alcohol solvent in the presence of a strong base. In addition, it has been shown that phenols can be alkylated by the reaction with a primary or secondary alkanol containing 2 or more carbon atoms in the presence of an alkali metal hydroxide at elevated temperatures and pressures.

U.S. Pat. No. 3,900,410 teaches that 2,6-di-tert-butyl-4-n-decylphenol can be synthesized by reacting 2,6-di-tert-butylphenol with n-decanol in the presence of KOH and a catalyst such as cupric oxide.

U.S. Pat. No. 3,919,333 teaches that 2,6-di-tert-butyl-4-n-decylphenol can be synthesized by reacting 2,6-di-tert-butylphenol with n-decanol in the presence of KOH but without the use of cupric oxide as a catalyst.

The products derived from the process of the present invention are not alkyl phenols but the more valuable and more difficult to obtain ω-hydroxy alkylated phenols. The terminal p-alkylhydroxy function imparts a much lower volatility to the phenol derivative than would the corresponding p-alkyl group. This is known to be an important factor in the retention of an antioxidant at elevated temperatures. Furthermore, the alkylhydroxy group offers a convenient functional handle to those skilled in organic synthesis for conversion to a wide variety of other potentially valuable compounds, e.g. esters, acids, etc.

DISCLOSURE OF INVENTION

The invention consists of a process for alkylating the nucleus of a phenol, said process comprising reacting an α,ω-alkanediol containing from 3 to 8 carbon atoms with a phenol having an unsubstituted nuclear position para to the phenolic hydroxyl group; said phenol being selected from the group of alkylated phenols having tertiary alkyl groups of 4 to 8 carbon atoms in both positions ortho to the phenolic hydroxyl group, in the presence of an alkali metal hydroxide or alkoxide or alkali metal at a temperature from 200° to 300° C. while continuously removing the water by-product as it forms and obtaining as a product said phenol having a primary hydroxy terminated alkyl group of 3 to 8 carbon atoms in said para position.

The simplest envisioned process to obtain alcohols of the structure:

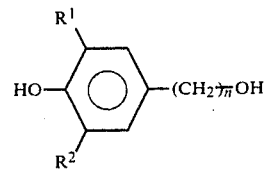

wherein $3 \leq n \leq 8$ would be one which gave the desired product in one step. This has now been accomplished via the following reaction.

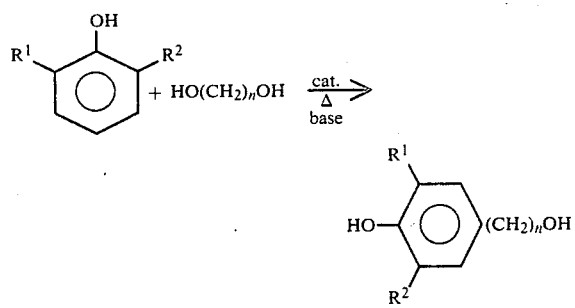

wherein $R^1$ and $R^2$ may be the same or different and are selected from the group comprised of tert.-alkyl groups containing from 4 to 8 carbon atoms which has been carried out under several sets of conditions.

A MORE DETAILED DESCRIPTION OF THE INVENTION

Attempts to alkylate phenols are disclosed in the references above. However, none of these references discloses or suggests the reaction of a phenol with an alkane diol containing 3 to 8 carbon atoms in the presence of an alkali metal hydroxide, alkoxide or alkali metal. Thus, it is evident that a process for the alkylation of phenols which provides a solution to the problems of: multi-step synthesis, high reaction pressures and temperatures, long reaction times and the use of co-catalysts, would be an advancement over what is presently known in the art. The process of this invention is especially useful for introducing a primary alkanol group and is operable on tert.-alkyl-substituted phenols without excessive dealkylation, as is encountered using an acidic catalyst. The process of this invention utilizes relatively low cost starting materials to obtain the substituted alkanols in one-step with reduced reaction times and less expensive reaction vessels.

The present invention is a process for alkylating the nucleus of a phenol, said process consisting essentially of reacting an alkane diol containing from 3 to 8 carbon atoms with a phenol having an unsubstituted position para to the phenolic hydroxyl group in the presence of an alkali metal hydroxide, metallic sodium or potassium, or an alkali metal alkoxide at a temperature of from 200° C. to 250° C. The process of this invention is applicable to phenols of the following structure:

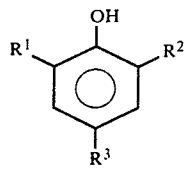

wherein R¹ and R² are tertiary alkyl groups of 4 to 8 carbons and R³ equals H.

Illustrative of the preferred phenols are:
2,6-di-tert.-butylphenol
2,6-di-tert.-pentylphenol
2,6-di-tert.-hexylphenol
2,6-di-tert.-heptylphenol
2,6-di-tert.-octylphenol
2-tert-butyl-6-tert.-pentylphenol
2-tert.-butyl-6-tert.-hexylphenol In a preferred embodiment the alkylphenol is a tertiary alkyl-phenol such as 2,6-di-tert.butylphenol,, 2,6-di-tert. hexylphenol and the like. The most preferred starting phenol is 2,6-di-tert.-butylphenol.

Useful α,ω-alkane diols contain from 3 to 20 carbon atoms. Especially useful alkane diols are those containing from 3 and up to about 8 carbon atoms. Of these the most preferred groups are the linear or normal alkane diols. Examples of useful alkane diols are 1,3-proponediol, 1,4-butanediol, 1,5-pentanediol, 1,7-heptanediol, 1,8-octanediol and the like.

The amount of alkane diol can vary over a wide range. A useful operating range is from 1 to 100 moles of alkane diols per mole of phenol. A preferred range is from 3 to 20 moles of alkane diol per mole of phenol, and a most preferred range is from 5 to 10 moles of alkane diol per mole of phenol.

When the amount of alkane diol relative to phenol is high it is preferred that the amount of base be likewise on the high side of the operative range.

The alkali metal hydroxides include lithium hydroxide, sodium hydroxide, potassium hydroxide and rubidium hydroxide. The more preferred are sodium hydroxide and potassium hydroxide with potassium hydroxide being the most preferred In addition, alkali metal alkoxides may be employed with the most preferred being sodium methoxide, sodium ethoxide, potassium methoxide, and potassium ethoxide. The alkali metals such as sodium and potassium may be used.

The amount of base can vary over a wide range. A useful operating range is from 0.05 to 1 mole of alkali metal hydroxide per mole of alkane diol. Preferably the amount of base is sufficient to form a saturated solution in the alkane diol and range from 0.2 to 1.0 mole of base per mole of phenol.

The process proceeds at elevated temperatures. A useful operating range is about 200° to 250° C. When the starting phenol is a 2,6-di-tertiary alkyl substituted phenol a preferred operating range is about 200° to 225° C.

The reaction is conducted by mixing the phenol, alkanediol, alkali metal hydroxide, metallic sodium or other base and heating the mixture. It is not necessary nor is it recommended to add an aldehyde or to use a co-catalyst such as a copper screen taught in U.S. Pat. No. 2,841,623.

The following examples serve to illustrate the manner in which the invention is conducted.

BEST MODE FOR CARRYING OUT THE INVENTION

EXAMPLE 1

Preparation of 6-(3,5-di-tert.-butyl-4-hydroxyphenyl) hexanol was conducted by fitting a 250 ml. flask with a water trap and charging the flask with 3.25 grams (0.05 mole) of powdered 86% potassium hydroxide. The flask was purged with nitrogen and there was then added a molten mixture of 19.8 grams of 2,6-di-tert.-butylphenol (0.096 moles) and 56.5 grams of 1,6-hexanediol (0.48 moles). The mixture was heated to 230°–235° C. for several hours during which 3.6 ml. of distillate was collected in the trap. The mixture was cooled to 50° C. and extracted with 200 ml. of toluene. The toluene layer was separated and reserved. The lower alcohol layer was extracted twice again with 200 ml. of toluene. The extracts were combined and washed with water. The toluene was removed under reduced pressure and the oily residue was vacuum distilled. There was obtained 18.9 grams of 6-(3,5-di-tert.butyl-4-hydroxyphenyl)hexanol which represents a 61.8% yield. The pot residue from the distillation, 4.3 grams, was recrystallized twice from acetone to yield 0.8 grams of 1,6-bis(3,5-di-tert.-butyl-4-hydroxyphenyl) hexane with a melting point of 147°–149° C.

EXAMPLE 2

Preparation of 5-(3,5-di-tert.-butyl-4-hydroxyphenyl) pentanol was conducted by adding 3.25 grams of powdered potassium hydroxide (0.05 moles) to 20.6 grams of 2,6-di-tert.-butyl phenol (0.1 moles) and 52 grams of 1,5-pentanediol (0.05 moles. The mixture was heated to 235° C. for 5.25 hours in an atmosphere of nitrogen in a 250 ml. flask fitted with a water trap. In the trap 4.2 ml. of distillate was collected during the heating period. The reaction mixture was worked up in the manner described previously in Example 1 and there was obtained 16.9 grams (58% yield) of 5-(3,5-di-tert.-butyl-4-hydroxyphenyl) pentanol, a pale yellow liquid with a boiling point of 140°–145° C. at 0.15 mm. of mercury.

When metallic sodium is used as the base in an atmosphere of nitrogen the reaction will not occur. However, in the presence of a trace amount of air, the reaction does take place, giving yields which are generally higher than those obtained by the procedure described in Example 2. Examples 3, 4, and 5 illustrate this method.

EXAMPLE 3

Preparation of 6-(3,5-di-tert.-butyl-4-hydroxyphenyl) hexanol. To 1.15 grams of metallic sodium (0.05 moles) was added to 59 grams of 1,6-hexanediol (0.5 moles) in a 250 ml flask fitted with a water trap and the mixture was stirred until the sodium dissolved. There was then added 20.6 grams of 2,6-di-tert.-butylphenol (0.1 mole) and the mixture was heated for 7.5 hours at 225° C. The mixture was allowed to cool and the base was neutralized by the addition of 5 ml. of concentrated hydrochloric acid. Sodium chloride from neutralization of the base was removed by filtration and the filtrate was distilled under vacuum. There was obtained 20.4 grams (66.6% yield) of 6-(3,5-di-tert.-butyl-4-hydroxyphenyl)-hexanol.

EXAMPLE 4

Preparation of 4-(3,5-di-tert.-butyl-4-hydroxy phenyl) butanol. Using 45 grams (0.5 moles) of 1,4-butanediol in place of the 1,6-hexanediol of Example 3 and heating the mixture for 5 hours yielded after workup 13 grams (47% yield) of 4-(3,5-di-tert.butyl-4-hydroxyphenyl)butanol.

EXAMPLE 5

Preparation of 3-(3,5-di-tert.-butyl-4-hydroxyphenyl) propanol. Substitution of 38 grams (0.5 moles) of 1,3-propanediol for the 1,6-hexanediol of Example 3 and heating the mixture for 5 hours yielded after workup 9.4 grams (35.5% yield) of 3-(3,5-di-tert.-butyl-4-hydroxyphenyl) propanol. The product is a pale yellow oil of a boiling point 135°–140° C. at 0.15 mm. of mercury which crystallized on standing to give a solid with a melting point of 67.5 to 69° C.

Experimental evidence indicates that the alkylation reaction proceeds by a free radical mechanism. Thus, a free radical source must be present to initiate the reaction. It appears that oxygen in the air serves as the radical source in Examples 3, 4 and 5.

It has been found that hydroperoxides can also serve as the source of free radicals for alkylation of phenols. In example 6 tert.-butyl hydroperoxide serves as the free radical source.

EXAMPLE 6

Preparation of 6-(3,5-di-tert.-butyl-4-hydroxyphenyl) hexanol. 1.15 grams of metallic sodium (0.05 moles) was added to 59 grams of 1,6-hexanediol (0.5 moles) in a 250 ml. flask fitted with a water trap and the mixture was stirred until the sodium dissolved. The flask was purged with nitrogen and there was then added 20.6 grams of 2,6-di-tert.-butylphenol (0.1 moles) and 0.5 grams (0.0055 moles) of tert.-butyl hydroperoxide. The mixture was heated at 230° C. for 5.5 hours with 0.5 gram increments of tert.-butyl hydroperoxide being added after 1, 2.5, 3.5, and 4.5 hours. The mixture was allowed to cool and was then neutralized by the addition of 5 ml. of concentrated hydrochloric acid. Sodium chloride from the neutralization of the base was removed by filtration and the filtrate was distilled under vacuum. There was obtained 18.5 grams 6-(3,5-di-tert.-butyl-4-hydroxyphenyl)hexanol, 60.5% yield.

Industrial Applicability

The products made by this process are useful antioxidants. For examples, 6-(3,5-tert.-butyl-4-hydroxyphenyl)hexanol is a stabilizer for polyethylene and other poly olefins such as polypropylene, SBR rubber and the like. A useful concentration in the organic substrate is from about .05 to 5 weight percent.

More important than the use of these products as anti-oxidants is the ability of the processes of this invention to yield compounds which heretofore were unobtainable except for expensive multi-step reactions. The products of this invention are prepared in reasonably good yields in one-step from relatively inexpensive starting materials. The products of this invention are also useful as precursors for the preparation of polymerizable antioxidants and high performance polyolefin stabilizers.

While certain representative embodiments and details have been shown for the purpose of illustrating the invention it will be apparent to those skilled in this art that various changes and modifications may be made therein without departing from the spirit or scope of the invention.

We claim:

1. A process for alkylating the nucleus of a phenol, said process comprising reacting an $\alpha,\omega$ alkanediol containing from 3 to 8 carbon atoms with a phenol having an unsubstituted nuclear position para to the phenolic hydroxyl group; said phenol being selected from the group of alkylated phenols having tertiary alkyl groups of 4 to 8 carbon atoms in both positions ortho to the phenolic hydroxyl group and in the presence of an alkali metal hydroxide or alkoxide or alkali metal at a temperature of 200°–250° C. at essentially ambient pressure with the removal of the water by-product, to obtain as a product said phenol having a primary hydroxy terminated alkyl group of 3 to 8 carbon atoms in said para position.

2. A process according to claim 1 wherein said phenol is 2,6-di-tert.butylphenol.

3. A process according to claim 1 wherein said alkanediol is 1,3-propanediol.

4. A process according to claim 1 wherein said alkanediol is 1,4-butanediol.

5. A process according to claim 1 wherein said alkanediol is 1,5-pentanediol.

6. A process according to claim 1 wherein said alkanediol is 1,6-hexanediol.

7. A process according to claim 1 wherein said alkanediol is 1,7-heptanediol.

8. A process according to claim 1 wherein the alkanediol is 1,8-octanediol.

9. A process according to claim 1 wherein said alkali metal hydroxide is sodium hydroxide.

10. A process according to claim 1 wherein said alkali metal hydroxide is potassium hydroxide.

11. A process according to claim 1 wherein the catalyst is an alkali metal and the process is conducted in an inert atmosphere and in the presence of a hydroperoxide.

12. A process according to claim 11 wherein the alkali metal is metallic sodium.

13. A process according to claim 11 wherein the hydroperoxide is tertiary butyl hydroperoxide.

* * * * *